United States Patent
Koroteev et al.

(10) Patent No.: US 9,599,551 B2
(45) Date of Patent: Mar. 21, 2017

(54) METHOD FOR ESTIMATING POROSITY OF A ROCK SAMPLE

(75) Inventors: Dmitry Anatolievich Koroteev, Moscow (RU); Alexander Nadeev, Spring, TX (US); Dmitry Alexandrovich Korobkov, Moscow (RU); Igor Andreevich Varfolomeev, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 63 days.

(21) Appl. No.: 14/406,696

(22) PCT Filed: Jun. 9, 2012

(86) PCT No.: PCT/RU2012/000453
§ 371 (c)(1),
(2), (4) Date: May 19, 2015

(87) PCT Pub. No.: WO2013/184021
PCT Pub. Date: Dec. 12, 2013

(65) Prior Publication Data
US 2015/0268149 A1  Sep. 24, 2015

(51) Int. Cl.
*G01N 33/24* (2006.01)
*G01N 7/00* (2006.01)
(Continued)

(52) U.S. Cl.
CPC ............ *G01N 15/08* (2013.01); *G01N 23/046* (2013.01); *G01N 23/083* (2013.01); *G01N 2015/0846* (2013.01)

(58) Field of Classification Search
CPC ........ G01N 23/046; G01N 33/24; G01N 7/00; G01N 15/088
(Continued)

(56) References Cited

U.S. PATENT DOCUMENTS 2,840,717 A   1/1958 Dewitte
4,562,726 A   1/1986 Barnaby
(Continued)

FOREIGN PATENT DOCUMENTS

GB   2414072 A   11/2005
RU   2444031 C2   2/2012

OTHER PUBLICATIONS

International Search Report for International Application No. PCT/RU2012/000453 dated Mar. 21, 2013, 2 pp.

*Primary Examiner* — David A Vanore

(57) ABSTRACT

A method for estimating porosity of a rock sample comprises the steps of defining a total mineral content of a sample, determining relative volume fractions for each mineral and determining X-ray attenuation coefficients for the defined minerals. Then, a first X-ray attenuation coefficient for a synthetic sample combined from the same minerals with the same volume fractions but with no pores is determined. X-ray micro/nanoCT scanning of the sample is performed and a second X-ray attenuation coefficient for the rock sample is determined. Porosity can be calculated as for a sample filled with a gas, water or light hydrocarbons, so for a sample which pores are filled with heavy hydrocarbons, or other liquid/gases with X-ray attenuation coefficient comparable with X-ray attenuation coefficient for the rock sample or for the synthetic sample.

10 Claims, 2 Drawing Sheets

(51) Int. Cl.
*G01N 15/08* (2006.01)
*G01N 23/083* (2006.01)
*G01N 23/04* (2006.01)

(58) Field of Classification Search
USPC .... 250/255, 253, 254, 256, 258, 264, 269.1; 378/4, 53, 5, 51, 54
See application file for complete search history.

(56) References Cited

U.S. PATENT DOCUMENTS

| | | | | |
|---|---|---|---|---|
| 4,982,086 | A * | 1/1991 | Withjack | G01N 33/24 250/255 |
| 5,058,425 | A * | 10/1991 | Davis, Jr. | G01N 7/00 250/254 |
| 5,164,590 | A * | 11/1992 | Coles | G01N 23/046 250/253 |
| 5,359,194 | A * | 10/1994 | Moss | G01N 15/08 250/255 |
| 5,430,291 | A * | 7/1995 | Pepin | G01N 15/088 250/255 |
| 5,984,023 | A * | 11/1999 | Sharma | E21B 47/00 175/40 |
| 8,068,579 | B1 | 11/2011 | Yun et al. | |
| 8,761,334 | B2 * | 6/2014 | Mikhailov | G01N 33/24 378/53 |
| 8,781,065 | B2 * | 7/2014 | Taylor | G01N 15/088 378/51 |
| 8,873,701 | B2 * | 10/2014 | Mikhailov | G01N 33/24 378/4 |
| 9,140,673 | B2 * | 9/2015 | Ferguson | G01N 29/30 |
| 2010/0135536 | A1 | 6/2010 | Dvorkin et al. | |
| 2014/0072095 | A1 * | 3/2014 | Feser | G01N 23/2206 378/4 |
| 2014/0100795 | A1 * | 4/2014 | Nadeev | G01N 25/005 702/23 |
| 2014/0334690 | A1 * | 11/2014 | Nadeev | G01N 15/0227 382/109 |
| 2016/0187509 | A1 * | 6/2016 | Boot | G01V 1/30 382/109 |

* cited by examiner

METHOD FOR ESTIMATING POROSITY OF A ROCK SAMPLE

This application is a U.S. National Stage Application of International Application No. PCT/RU2012/000453, filed Jun. 9, 2012.

FIELD OF THE INVENTION

The invention relates to X-ray based analysis of a core sample, namely microtomography (microCT) and nanotomography (nanoCT) techniques.

BACKGROUND OF THE INVENTION

In oilfield industry porosity is the key value for determining the amount of hydrocarbon resources for a particular reservoir. There are a number of methods for measuring porosity of core samples. Standard ones include gas saturation with pressure-volume control, liquid saturation with weighting, petrographic analysis of thin sections (see for example U.S. Pat. No. 4,562,726, U.S. Pat. No. 2,840,717). Main disadvantage of listed methods is that they are relatively time consuming and operator dependent. Petrographic analysis of thin sections might provide absolutely non-representative results as it deals with finite number (usually 1 or 2) of 2D sections of the real 3D rock sample. Preparation of these sections might be destructive and this decreases the adequacy of 2D thin section porosity interpretation even more.

SUMMARY OF THE INVENTION

A method that allows fast, non-destructive, and operator-independent estimation of porosity inside a rock sample is proposed. Unlike the petrographic analysis the proposed method accounts for real 3D structure of porous space of the rock sample.

The method for estimating porosity of a rock sample comprises the steps of defining a total mineral content of a sample, determining relative volume fractions for each mineral and determining X-ray attenuation coefficients for the defined minerals. A first X-ray attenuation coefficient for a synthetic sample combined from the same minerals with the same volume fractions but with no pores is determined. Then, X-ray micro/nanoCT scanning of the sample is performed and a second X-ray attenuation coefficient for the rock sample is determined.

If pores of the sample are filled with a gas, water or light hydrocarbons, porosity of the sample is calculated as $$P = 1 - \frac{K}{K_s}$$

or if pores of the sample are filled with heavy hydrocarbons, or other liquid/gases with X-ray attenuation coefficient comparable with K or $K_s$, porosity of the sample is calculated as $$P = \frac{K_s - K}{K_s - K_l}$$

where P—porosity of the sample, $K_s$—the first X-ray attenuation coefficient for the synthetic sample, K—the second X-ray attenuation coefficient for the rock sample, $K_l$—X-ray attenuation coefficient for the liquid/gas inside the pores of the sample.

Total mineral content of the sample and relative volume fractions of each mineral can be defined using one of the conventional methods: thin section petrography analysis, Micro X-ray fluorescence (XRF), powder/single crystal X-ray diffraction (XRD), Raman microscopic imaging, scanning electron imaging with further X-ray spectra analysis.

X-ray attenuation coefficients for the defined minerals can be determined by microCT scanning of single grains of each mineral and performing regression analysis of intensity profile along the horizontal line at the projection microCT image VS grain thickness profile along the corresponding line in corresponding reconstructed microCT slice or by using database of X-ray attenuation coefficients.

The second X-ray attenuation coefficient for the rock sample can be determined by performing regression analysis of intensity profile along the horizontal line at the projection microCT image versus grain thickness profile along the corresponding line in corresponding reconstructed microCT slice.

DETAILED DESCRIPTION OF THE INVENTION

Figure 1:
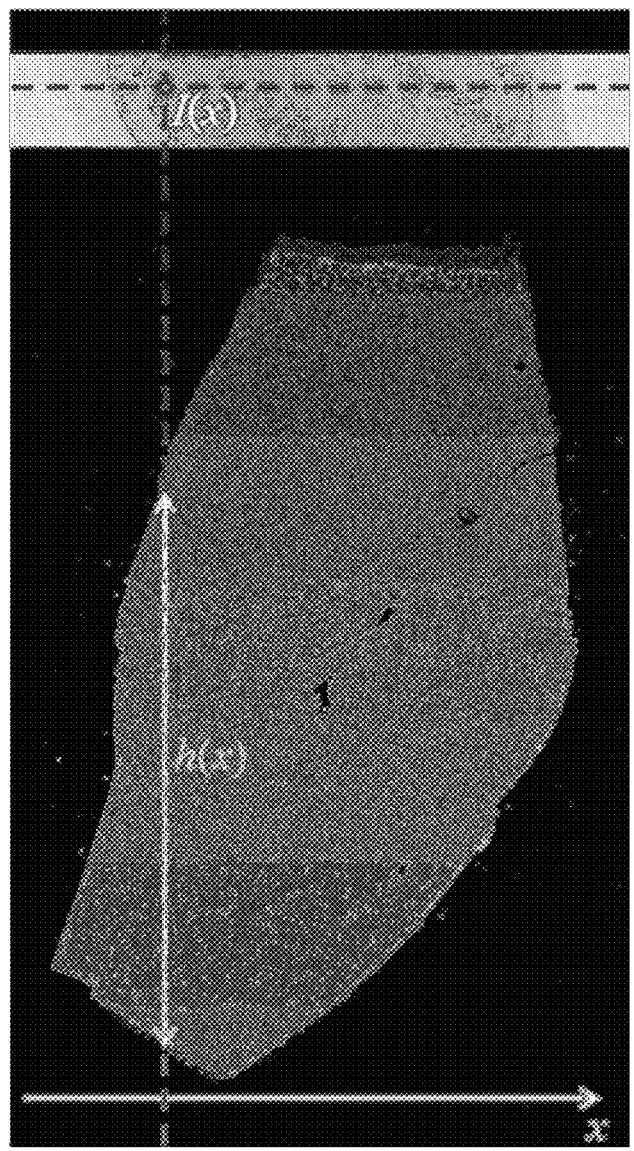
FIG. 1 illustrates measuring the exact value of an attenuation coefficient of single grain of calcite.

Different minerals have different chemical content (chemical elements) and density. In the other words, the minerals possess different contrast in X-ray projection and might be differentiated by their X-ray absorption (linear attenuation) coefficients:

$$I = I_0 e^{-\mu l}$$

where I—X-ray intensity after passing a layer of a matter with thickness l, $I_0$—initial X-ray intensity, $\mu$—linear attenuation coefficient (usually measured in $cm^{-1}$). This feature allows expecting different grayscale levels which correspond to volumes occupied by grains of different minerals in 3D micro/nanoCT image of a rock sample. Having known what minerals ($M_1, M_2, \ldots, M_n$) dominate in the sample, it is possible to estimate the values of X-ray attenuation coefficient for them ($k_1, k_2, \ldots, k_n$).

The method comprises the following steps. At first, total mineral content of the sample $M_1, M_2, \ldots, M_n$ and relative volume fractions for the defined minerals $G_1, G_2, \ldots, G_n$ are determined using one of the known methods—petrography (see, for example, www.ncptt.nps.gov/digital-image-analysis-of-petrographic-thin-sections-in-conservation-research-2004-01), Micro-X-ray fluorescence (XRF) (see, for example, www.horiba.com/fileadmin/uploads/Scientific/Documents/XRay/xgtmin01.pdf), powder/single crystal X-ray diffraction (XRD) (see, for example, Ore Geology Reviews, Volume 6, Issues 2-3, May 1991, Pages 107-118, Applied Mineralogy in Exploration), Raman microscopic imaging (see, for example http://www.witec-instruments.de/en/download/Raman/Geoscience.pdf), scanning electron imaging with further X-ray spectra analysis (see, for example, http://www.fei.com/applications/industry/).

Petrography (optical mineralogy) is the study of minerals and rocks by measuring their optical properties. Most commonly, rock and mineral samples are prepared as thin sections or grain mounts for study in the laboratory with a petrographic microscope. Optical mineralogy is used to identify the mineralogical composition of geological materials in order to help reveal their origin and evolution (see www.ncptt.nps.gov/digital-image-analysis-of-petrographic-thin-sections-in-conservation-research-2004-01).

X-ray fluorescence (XRF) is the emission of characteristic "secondary" (or fluorescent) X-rays from a material that has been excited by bombarding with high-energy X-rays or gamma rays. The phenomenon is widely used for elemental analysis and chemical analysis, particularly in the investigation of metals, glass, ceramics and building materials, and for research in geochemistry, forensic science and archaeology.

The example of XRF application for geosamples can be found here: http://www.horiba.com/fileadmin/uploads/Scientific/Documents/XRay/xgtmin01.pdf.

The Confocal Raman microscopes record a Raman spectra at each pixel of 2D area of a sample within a field of view. Decoding the spectra gives the chemical compound in the pixel. In case of natural rocks, areas with same chemical compounds are then assigned to different minerals (see http://www.witec-instruments.de/en/download/Raman/Geoscience.pdf).

X-ray diffraction yields the atomic structure of materials and is based on the elastic scattering of X-rays from the electron clouds of the individual atoms in the system. The most comprehensive description of scattering from crystals is given by the dynamical theory of diffraction. Powder diffraction (XRD) is a technique used to characterise the crystallographic structure, crystallite size (grain size), and preferred orientation in polycrystalline or powdered solid samples. Powder diffraction is commonly used to identify unknown substances, by comparing diffraction data against a database maintained by the International Centre for Diffraction Data (XRD analysis—Ore Geology Reviews, Volume 6, Issues 2-3, May 1991, Pages 107-118, Applied Mineralogy in Exploration).

Energy-dispersive X-ray spectroscopy (EDX) is an analytical technique used for the elemental analysis or chemical characterization of a sample. It is one of the variants of X-ray fluorescence spectroscopy which relies on the investigation of a sample through interactions between electromagnetic radiation and matter, analyzing X-rays emitted by the matter in response to being hit with charged particles. Its characterization capabilities are due in large part to the fundamental principle that each element has a unique atomic structure allowing X-rays that are characteristic of an element's atomic structure to be identified uniquely from one another. EDX systems are most commonly found on scanning electron microscopes (SEM-EDX) and electron microprobes. Scanning electron microscopes are equipped with a cathode and magnetic lenses to create and focus a beam of electrons, and since the 1960s they have been equipped with elemental analysis capabilities. A detector is used to convert X-ray energy into voltage signals; this information is sent to a pulse processor, which measures the signals and passes them onto an analyzer for data display and analysis (http://www.fei.com/applications/industry/)

X-ray attenuation coefficients $k_1, k_2, \ldots, k_n$ for all defined minerals $M_1, M_2, \ldots, M_n$ are determined. The estimation for X-ray attenuation coefficients might be performed by microCT scanning of single grains of each mineral and performing regression analysis of intensity profile along the horizontal line at the projection microCT image versus grain thickness profile along the corresponding line in corresponding reconstructed microCT slice [http://www.skyscan.be/company/UM2011/abstract_08.pdf] or by using NIST database, for example (http://www.nist.gov/pml/data/xraycoef/index.cfm).

High resolution micro/nanoCT experiment with the sample is performed and the 3D micro/nanoCT image in gray scale is obtained.

Then, a first X-ray attenuation coefficient for synthetic sample $K_s$ combined from the same minerals as determined in the sample with the same volume fractions but with no pore is calculated:

$$K_s = G_1 k_1 + G_2 k_2 + \ldots + G_n k_n$$

Figure 2:
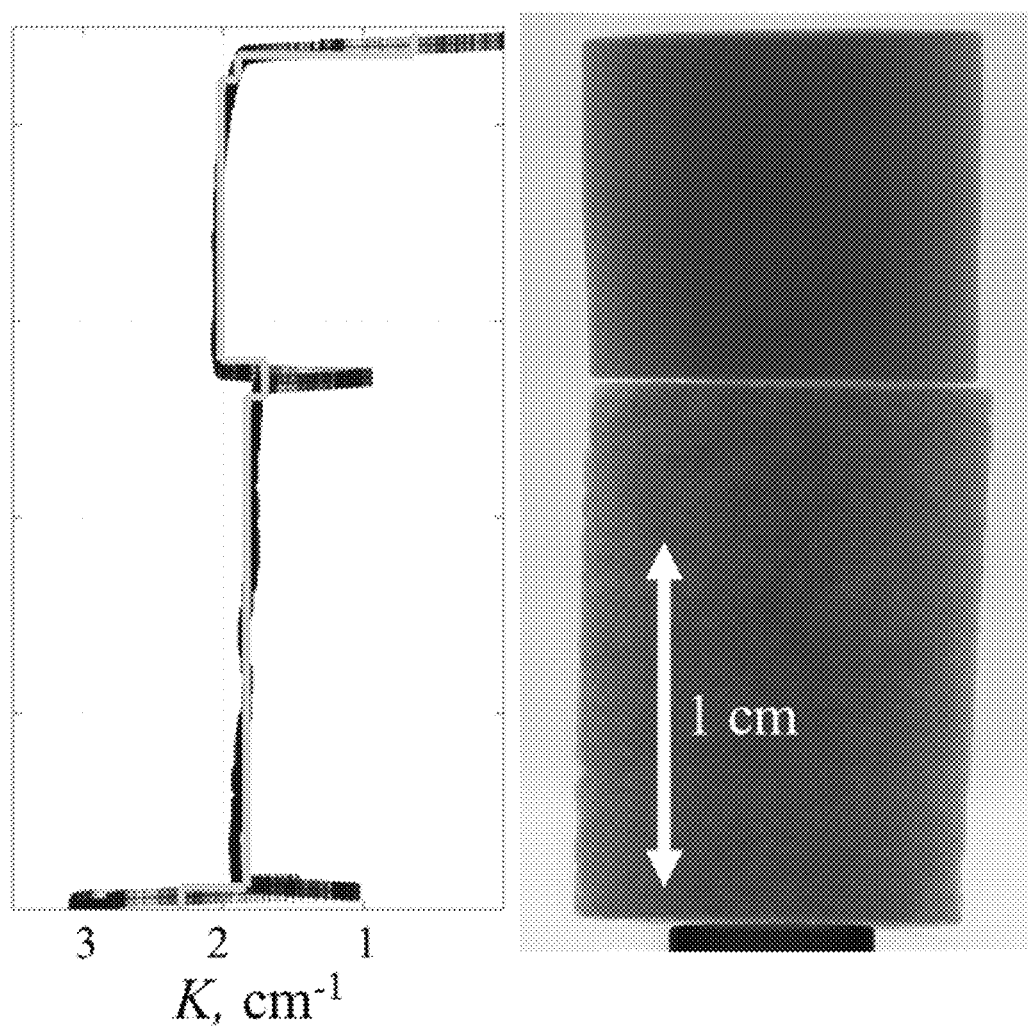
FIG. 2 shows distribution of the attenuation coefficients along two rock samples.

MicroCT scanning of the sample is performed and the second X-ray attenuation coefficient K for the whole rock sample is determined. It can be determined, for example, by performing regression analysis of intensity profile along the horizontal line at the projection microCT image versus grain thickness profile along the corresponding line in corresponding reconstructed microCT slice (see FIG. 2, where right plane represents an X-ray projection image of two carbonate samples with different porosities (one on a top of another)).

If pores of the sample are filled with a gas, water or light hydrocarbons, the sample's porosity can be calculated as $$P = 1 - \frac{K}{K_s},$$

and if the pores of the sample are filled with heavy hydrocarbons, or other liquid/gases with X-ray attenuation $K_l$ comparable with K or $K_s$ the sample's porosity can be calculated as $$P = \frac{K_s - K}{K_s - K_l}$$

$K_l$ might be determined by microCT scanning of single grains of each mineral and performing regression analysis of intensity profile along the horizontal line at the projection microCT image versus grain thickness profile along the corresponding line in corresponding reconstructed microCT slice [http://www.skyscan.be/company/UM2011/abstract_08.pdf] or by using NIST database, for example (http://www.nist.gov/pml/data/xraycoef/index.cfm).

The invention claimed is:

1. Method for estimating porosity of a rock sample, comprising:
   defining total mineral content of the sample and relative volume fractions for each mineral;
   determining X-ray attenuation coefficients for the defined minerals,
   calculating a first X-ray attenuation coefficient for a synthetic sample combined from the same minerals as defined in the sample with the same volume fractions but with no pores,
   performing X-ray microCT scanning of the sample;
   determining a second X-ray attenuation coefficient for the sample,
   calculating porosity of the sample as $$P = 1 - \frac{K}{K_s}$$

if pores of the sample are filled with a gas, water or light hydrocarbons, or as $$P = \frac{K_s - K}{K_s - K_l}$$

if pores of the sample are filled with heavy hydrocarbons, or other liquid/gases with X-ray attenuation coefficient comparable with K or $K_s$, where P—porosity of the sample, $K_s$—the first X-ray attenuation coefficient for the synthetic sample, K—the second X-ray attenuation coefficient for the rock sample, $K_l$—X-ray attenuation coefficient for the liquid/gas inside the pores of the sample.

2. The method of claim 1 wherein mineral content of the sample and relative volume fractions for the defined minerals are defined by petrography analysis.

3. The method of claim 1 wherein mineral content of the sample and relative volume fractions for the defined minerals are defined by X-ray fluorescence.

4. The method of claim 1 wherein mineral content of the sample and relative volume fractions for the defined minerals are defined by X-ray diffraction.

5. The method of claim 1 wherein mineral content of the sample and relative volume fractions for the defined minerals are defined by Raman microscopic imaging.

6. The method of claim 1 wherein mineral content of the sample and relative volume fractions for the defined minerals are defined by scanning electron imaging with further X-ray spectra analysis.

7. The method of claim 1 wherein X-ray attenuation coefficients for the defined minerals are determined by microCT scanning of single grains of each mineral and performing regression analysis of intensity profile along the horizontal line at the projection microCT image VS grain thickness profile along the corresponding line in corresponding reconstructed microCT slice.

8. The method of claim 1 wherein X-ray attenuation coefficients for the defined minerals are determined from database of X-ray attenuation coefficients.

9. The method of claim 1 wherein the second X-ray attenuation coefficient for the rock sample is determined by performing regression analysis of intensity profile along the horizontal line at the projection microCT image versus grain thickness profile along the corresponding line in corresponding reconstructed microCT slice.

10. The method of claim 1 wherein the X-ray attenuation coefficient for the liquid/gas inside the pores of the sample is determined from database of X-ray attenuation coefficients.

* * * * *